US005753592A

United States Patent [19]
Mintz et al.

[11] Patent Number: 5,753,592
[45] Date of Patent: May 19, 1998

[54] ACREMONIUM MYCOHERBICIDE FOR BIOCONTROL OF DANDELION

[75] Inventors: Angel Mintz, Raleigh, N.C.; James F. Walter, Ashton, Md.

[73] Assignee: Thermo Trilogy Corporation, Waltham, Mass.

[21] Appl. No.: 773,923

[22] Filed: Dec. 30, 1996

[51] Int. Cl.[6] .............................. A01N 63/04; C12N 1/14
[52] U.S. Cl. ..................... 504/117; 435/256.4; 435/926
[58] Field of Search ..................... 504/117; 435/256.4, 435/926

[56] References Cited

U.S. PATENT DOCUMENTS

| | | | |
|---|---|---|---|
| 4,097,261 | 6/1978 | Conway et al. | 71/66 |
| 4,808,207 | 2/1989 | Gotlieb et al. | 71/73 |
| 5,538,890 | 7/1996 | Sands et al. | 435/254.1 |

*Primary Examiner*—S. Mark Clardy
*Attorney, Agent, or Firm*—Quarles & Brady

[57] ABSTRACT

Spores of a biocontrol fungus, Acremonium sp. ATCC 74368, have been found to function well as a biocontrol agent in a method for biocontrol of dandelion (*Taraxacum officinale*).

4 Claims, No Drawings

ACREMONIUM MYCOHERBICIDE FOR BIOCONTROL OF DANDELION

BACKGROUND OF THE INVENTION

The present invention relates generally to biocontrol fungi and more specifically to fungi useful in controlling dandelions. Biological control of many plant species using microorganisms and compounds isolated therefrom is known. In U.S. Pat. No. 4,755,207, phytotoxic *Alternaria cassiae* spores were formulated and applied to sicklepod. In U.S. Pat. No. 4,209,826, *Amphbotrys ricini* was used successfully as a mycoherbicide against texasweed. In U.S. Pat. No. 4,606,751, *Bipolaris sorghicola* spores were demonstrated to kill johnson grass.

Certain unsuccessful efforts have been undertaken to identify and obtain biological agents, notably fungal phytopathogens, having phytotoxic activity against dandelions. Dandelions, classified as *Taraxacum officinale*, are common and persistent broadleaf weeds with wide geographic range. Dandelions are listed as the most important turf weeds in the U.S. in more states (42) than any other dicotyledon. To date, dandelions have been uncontrolled under typical environmental conditions except by mechanical means or with chemical herbicides which are disfavored because of their toxicity to humans and animals and to beneficial plants. The most common chemical herbicide used to control dandelions is the fungicide 2,4-D, which has been shown to contain dioxins in certain formulations and which may be a human carcinogen. Other known chemical herbicides effective against dandelions include Basagran and Round-Up.

Several biocontrol agents have been ineffective against dandelion growth. For example, in U.S. Pat. No. 4,390,360, an *Alternaria cassiae* fungus selected for biological control of a number of plant weeds was demonstrated to be ineffective against dandelions. Likewise, U.S. Pat. No. 4,929,270 discloses that compounds isolated from a fungal pathogen of spotted knapweed were selectively phytotoxic against knapweed, but spared dandelions and a number of other dicots and monocots. The effective target range of most mycoherbicides is narrow and, to date, biological control of dandelions has not been readily accomplished.

A mutated strain of *S. sclerotiorum* for controlling dandelions has been patented. Riddle, G.E., et al., Weed Science 39:109–118 (1991), showed in certain isolates of *Sclerotinia sclerotiorum* and *S. minor* a positive correlation between virulence on dandelion leaves and reduction in amount of dandelion foliage or number of dandelion plants. However, *S. sclerotiorum* is a soil-borne fungus having a different host range than the fungus of the present invention.

Other fungal isolates have been described which show activity against dandelions under conditions of extremely high humidity not typically encountered in temperate climates.

What is desired is a biological agent that is toxic to dandelions under typical environmental conditions but is non-toxic to humans, animals and desired plants.

BRIEF SUMMARY OF THE INVENTION

The present invention is summarized in that an Acremonium fungus that can been cultured as a substantially pure preparation exhibits good control of dandelion growth. The Acremonium fungus, Acremonium spp., AM 18, deposited with the American Type Culture Collection, 12301 Parklawn Drive, Rockville, Md. 20852, and accorded ATCC accession number 74368, is characterized and identified below.

The present invention is also directed toward a method for controlling dandelions using the novel fungus.

It is an object of the present invention to provide a phytotoxic biocontrol agent that effectively controls dandelion growth.

It is another object of the present invention to effectively control dandelion growth without using non-biological chemical agents.

It is an advantage of the present invention that the use of non-biological chemical agents is avoided.

It is a further advantage of the present invention that the phytotoxic fungus identified herein can be 100% effective at relatively low dosages to control dandelions and appears to have no toxicity against other plants or animals.

It is another advantage of the present invention that the fungus is readily reproduced and stored for subsequent use.

Other objects, features and advantages of the present invention will become apparent from the following specification.

DETAILED DESCRIPTION OF THE INVENTION

A novel fungal strain of Acremonium that exerts biological control over dandelion plant species was isolated from diseased dandelions and was grown and maintained in substantially pure cultures. Acremonium spp., AM 18 (ATCC 74368) was one of several fungi isolated from severely diseased dandelions in Howard County, Maryland. The symptoms of the diseased dandelions included leaf lesions and severe stem necrosis. The fungus sporulates abundantly in culture on PJA or DYA agar plates, producing numerous small conidia. This fungus can also be grown to produce conidia in liquid culture using simple substrates. The strain has been deposited in the American Type Culture Collection under the designation ATCC 74368 and shall hereinafter be referred to as "Acremonium sp. ATCC 74368" or simply as "ATCC 74368".

A "substantially pure" culture shall be deemed a culture of a fungus containing no other fungal species in quantities sufficient to interfere with replication of the desired fungus. "Biological control" or "biocontrol" is defined as control of dandelion plant growth by the use of a second organism. "Biological control" of dandelions shall be deemed to exist when a statistically significant increase in plant disease or mortality occurs after an effective quantity of the substantially pure culture is applied to the treated plant. A change in plant disease or mortality is measured on the scale of 0–5 described below in connection with the plant disease or mortality assay. An "effective quantity" shall be that quantity of the fungus sufficient to result in a significant increase in disease or mortality in treated plants, measured in the plant disease and mortality assay. Plants, including seeds, seedlings, and mature plants, that respond to an effective quantity of a fungus or toxin shall be referred to as "susceptible" to the fungus or toxin. Clearly, if no quantity of a fungus or any toxin or other compound is an effective quantity as so defined, that fungus, toxin, or compound is not capable of exerting biological control over the dandelion.

It is envisioned that certain mutants of ATCC 74368 can also be isolated that also provide biological control comparable or superior to that provided by ATCC 74368. Phytotoxic mutants of ATCC 74368 can include both naturally occurring and artificially induced mutants. Other such controlling mutants of ATCC 74368 can be artificially induced by subjecting ATCC 74368 to the mutagen, N-methylnitrosoguanidine in conventional ways. ATCC 74368 and those mutants capable of exerting such biological control shall sometimes be referred to collectively as "phytotoxic" fungi. Any mutant that retains effective biocontrol properties is within the scope of the present invention. It is likely that other such phytotoxic Acremonium strains that exert biological control over dandelions, as well as members of related genera such as Cephalosporium, will be isolated.

It is further envisioned that the fungus or mutants thereof may be genetically altered by the addition or removal of genes that affect fungal growth. In particular, for example, it is believed that introduction into the fungus of genetic material that confers resistance to an herbicide or to a biocontrol agent will make the fungus an excellent candidate for co-delivery with such an herbicidal agent to a cultivated area. In that case, the herbicide would be effective against other undesirable weeds and the fungus would be effective against the dandelion.

It is contemplated that the phytotoxic activity for each individual pathogenic fungus varies over a significant range. Accordingly, the amount of a particular fungus necessary to control dandelion growth can be determined empirically by in vitro studies of the type described herein. Based on such studies, an "effective amount" can readily be determined for a particular treating organism.

The biological effect of the fungus on the dandelion plant appears to be systemic. It is envisioned that the fungus is itself a parasite, or produces a phytotoxin having biocontrol activity. If one or more phytotoxins exist, they will be prepared in isolation from the phytotoxic fungi and will be characterized chemically so as to be identifiable independent of its source in cultures of ATCC 74368, or phytotoxic mutants thereof. It is specifically envisioned that any phytotoxin or phytotoxins responsible for biocontrol of dandelions are not unique to ATCC 74368 or its phytotoxic mutants, and, therefore, that a wide variety of other fungal organisms that do not derive from ATCC 74368 but which contain such a phytotoxin or phytotoxins could also be isolated. A phytotoxin could be isolated from ATCC 74368 or from its controlling mutants or other fungus by filtering the fungi from the culture media in which they have been grown. Alternatively, the phytotoxin could be isolated from the fungi rather than from their culture media, if the toxin is not secreted. Other conventional purification and concentration steps may then be undertaken as may be considered convenient or desirable, so long as the toxin remains active, as may be demonstrated by the plant disease and mortality assay (described below) that was initially developed to test plant protection activity observed using ATCC 74368. It is believed that the same assay can be used to test other candidate fungal strains for biocontrol activity.

The phytotoxin, if any, may readily be isolated from biocontrolling fungi which produce them by recovering the supernatant from sporulating colonies of the microorganisms. The supernatant, as described above, can be fractionated in a column and then separated by electrophoresis to identify the fractions which exhibit the biocontrol activity. Using high voltage paper electrophoresis, or comparable purification technique, the bioactive molecules can readily be repeatably recovered.

Based upon the observed biocontrol properties of the fungus, the following is a disclosure of a suitable plant disease and mortality assay whereby a test material such as a fungus, a phytotoxin, an extract or the like, may be tested for its ability to exert biological control over a dandelion. The seed of the dandelion plant to be controlled is planted in a planting medium. The planting medium can be vermiculite in water or any other planting medium in which the seed will grow and develop to an age of four weeks or less. The test material is sprayed onto the plant to runoff at a concentration of between $10^6$ and $10^7$ conidia/ml. The plant should be kept initially for at least 12 hours with free moisture and then maintained for up to one week at a temperature between 24° and 28° C. before evaluating disease and mortality as described above. Control plants sprayed only with water should be included in the assay. Mortality of plants treated with an effective fungal agent will be readily apparent when compared to controls, the growth of which should be unimpeded under these conditions. It is understood that an equally valid test for biocontrol may be performed on uncultivated dandelion plants growing naturally, taking into consideration the guidance of this specification as to temperature, dew period and plant age.

The following is a suitable disease rating scale for use in conjunction with the assay:

0=no disease
1=1–25% leaf necrosis
2=26–50% leaf necrosis
3=51–75% leaf necrosis
4=76–99% leaf necrosis
5=dead plant.

A fungal isolate (or phytotoxin isolated therefrom, or structurally-related phytotoxin) effective for biocontrol of *Taraxacum officinale* can be formulated as a biocontrol agent as follows. The fungus can be added to an inert carrier such as bentonite, silica, or alumina, or to a nutritive agent such as bran, corn cobs, newspaper, sawdust, or the like. Combinations of nutrients and inert carriers are preferred. The formulation can be granular (for broadcast application) or sprayable (in connection with a hose-end or pump sprayer). Liquid formulations containing the fungus comparable to formulations prepared for other biocontrol agents may also be used. The formulation can vary, in ways known to the art, depending upon whether the fungus is to be used preventively or curatively.

ATCC 74368, its phytotoxic mutants, other strains that exert biological control over dandelions, inocula containing ATCC 74368, its phytotoxic mutants or other biocontrolling strains, or one or more phytotoxins produced by, isolated from or structurally identical or equivalent thereto, and combinations thereof are all intended to fall within the scope of the present invention. Likewise, methods for preparing biocontrol agents, and methods for exerting biological control on dandelion growth, which employ ATCC 74368,its phytotoxic mutants, other biocontrolling strains, inocula containing ATCC 74368 or its mutants, or one or more phytotoxins produced by, isolated from or structurally identical or equivalent thereto, or combinations thereof are also within the scope of the present invention.

It is also envisioned that ATCC 74368, as well as a phytotoxin or phytotoxins present in ATCC 74368, may have comparable biocontrol activity against certain other related broadleaf weed plants, including other dandelion species. The fungus has no apparent biocontrol activity against grasses.

The invention will be more fully appreciated upon consideration of the following non-limiting Examples.

EXAMPLES

Fungi were collected in Howard County, Maryland from severely diseased flowering dandelions and from plants with seedheads. The symptoms of the diseased dandelions included leaf lesions and severe stem necrosis. Isolations were made to potato-dextrose agar (PDA) with kanamycin. Organisms recovered included Colletotrichum, Alternaria, Fusarium, Epicoccum, Cladosporium, a cleistothecial and a perithecial fungus, a yeast, and an Acremonium.

To determine whether any of the isolates had phytotoxic activity, dandelions with seedheads growing outside were drenched with a mixture of the Acremonium, the yeast, and the Colletotrichum, each at about $1\times10^6$ spores per ml. After about five days, the dandelions were severely diseased. Fungi recovered from the diseased dandelions included the Acremonium, Alternaria, Epicoccum, Fusarium and Cladosporium.

Next, six 4×6 inch trays were potted with Redi-earth and were seeded with dandelions. After about 3 weeks, plants were inoculated with either the Colletotrichum at $1\times10^6$ spores/ml or the Acremonium at about $1\times10^7$ spores/ml. Both spore suspensions were from PDA+kanamycin plates that had been incubated at room temperature with no specific light requirements for 12 days. The spores were rinsed from an actively growing culture using distilled water. The spore concentration was determined using a hemocytometer. A total of 35 ml of inoculant were used for each fungus. Two flats, each containing 5 dandelion plants (approximately 3 weeks old) (for a total of 10 treatments) were also inoculated for each treatment. Two control flats were sprayed only with water. After inoculation, plants were incubated at 24°–25° C. with a 12 hour photoperiod and a 24 hour dew period. The Acremonium infected all tested plants, killed 40% of the plants, and caused significant damage to those that survived. The damaging effects included severe stem necrosis, leaf curling, leaf lesions, stunted growth and death. Plants inoculated with the Colletotrichum were not killed, but leaves did develop lesions.

Two separate Acremonium isolates (#1429 and #1430) and the yeast thus obtained were more rigorously assessed for their ability to exert biological control against dandelion. The yeast isolate was soon thereafter determined to be non-pathogenic and was not evaluated further. All cultures were maintained in cryogenic storage (–80° C.). Subcultures were made directly from the cryogenic cultures for each experiment after it was determined that virulence declined and was lost after several culture transfers on agar medium. Isolates 1429 and 1430 caused significant plant mortality on 3–4 week old dandelion plants within one week of inoculation. In early experiments, most plants were killed within 48 hours. Although both isolates were determined to be equally pathogenic, isolate 1429 was used in all subsequent studies.

In these experiments, dandelion was seeded directly into plastic pots containing vermiculite and was grown for 3–4 weeks (to the 4–6 leaf stage) in lighted growth chambers at 28° C. (14 hour photoperiod). Each pot was thinned to 3–6 plants per pot after plant emergence. Plants were examined daily and were rated for disease seven days after treatment. Each plant was rated separately and the average rating for each pot was used for comparison in this plant disease and mortality assay. The disease rating scale was as noted above.

Dew period and dew temperature can influence plant infection. To determine the influence of these factors, conidia were harvested from 4–5 day old PDA plates and were standardized at $1\times10^6$ conidia/ml using a hemocytometer. Plants were sprayed to runoff and placed immediately into a dark dew chamber at 28° C. for 24 hours unless indicated otherwise.

To determine the dew period requirement, plants were placed into a dew chamber for 0, 4, 8, 12, 16, 20, or 24 hours at 28° C. Results of these tests are shown in Table 1. At least approximately 12 hours of free moisture were required for effective weed control using ATCC 74368. After 8 hours, plants showed moderate levels of leaf necrosis but plant mortality was limited.

TABLE 1

Influence of dew period on infection and disease development

| Dew Period (hr) | Disease Rating (0–5) | Mortality (%) |
|---|---|---|
| 0 | 0.8 | 0 |
| 4 | 0.6 | 0 |
| 8 | 2.4 | 18 |
| 12 | 4.5 | 72 |
| 16 | 4.9 | 90 |
| 20 | 4.9 | 97 |
| 24 | 4.9 | 97 |

To determine the influence of dew period temperature, pots were incubated for 24 hours in separate dew chambers adjusted to 16°, 20°, 24°, 28°, 32° or 36° C. Following incubation in the dew chamber, pots were placed into lighted growth chambers at 28° C. (14 Hour photoperiod) for the remainder of the experiment. Each experimental treatment included four pot replicates. Controls included one or more pots sprayed with water. As is reported in Table 2, significant disease development and plant mortality occurred at dew temperatures between 24° and 28° C. Disease development was limited at 20° and 32° C. Significant plant mortality was observed at 36° C., but this was attributed to heat stress rather than to any fungal phytotoxicity.

Several attempts were made to determine the influence of post-inoculation temperature on disease development. However, susceptible plants were killed so rapidly under disease-conducive conditions that this proved difficult to determine and the experiments were discontinued.

TABLE 2

Influence of dew temperature on infection and disease development

| Dew Temperature (hr) | Disease Rating (0–5) | Mortality (%) |
|---|---|---|
| 16 | 1.4 | 10 |
| 20 | 1.8 | 4 |
| 24 | 4.4 | 63 |
| 28 | 4.9 | 95 |
| 32 | 1.1 | 0 |
| 36 | 3.2 | 35 |

To determine the preferred inoculation dose, various concentrations of conidia in the range of $10^4$ to $10^7$ were prepared by serial dilution and were inoculated to runoff onto susceptible four-week old plants under disease conducive conditions of temperature and dew period. Plants were placed into a dew chamber at 28° C. (14 hour photoperiod). Each experimental treatment included five pot replicates. Plants were rated for disease seven days after inoculation. At a concentration of $10^6$ or greater, excellent control of dandelion plants was observed. At concentrations of $10^5$ or lower, disease development was limited and no mortality was observed, as is shown in Table 3.

TABLE 3

Influence of conidial concentration on infection and disease development

| Conidial Concentration | Disease Rating (0–5) | Mortality (%) |
|---|---|---|
| $10^4$ | 0 | 0 |
| $10^5$ | 1.0 | 0 |
| $10^6$ | 5.0 | 100 |
| $10^7$ | 5.0 | 100 |

To determine the influence of plant age on infection and disease severity, five pot replicates were seeded at weekly intervals for six weeks. Plants were sprayed to runoff with a conidial suspension of $1 \times 10^6$ conidia/ml when plants had reached ages of 2, 3, 4, 5, 6, and 7 weeks. In general, plants four weeks old (with 4–6 true leaves) or less were highly susceptible to the pathogen and were readily killed under conditions favorable for infection and disease development. Although numerous pinpoint lesions developed on older plants and older infected leaves collapsed, plants usually were not killed and grew out of the infection. This experiment was repeated several times with similar results although the exact cutoff point between plants with significant mortality and those without varied somewhat depending upon experimental conditions.

TABLE 4

Influence of plant age on susceptibility

| Plant Age (wk) | Disease Rating (0–5) | Mortality (%) |
|---|---|---|
| 2 | 5.0 | 100 |
| 3 | 5.0 | 100 |
| 4 | 3.0 | 90 |
| 5 | 2.0 | 0 |
| 6 | 1.0 | 0 |
| 7 | 1.0 | 0 |

In summary, excellent biological control of young dandelion plants was obtained within seven days of inoculation of ATCC 74368 under disease-conducive conditions. Mortality was often observed within 48 hours. These mortality results are comparable or superior to chemical weed control agents. Susceptible plants were rapidly killed following at least 12 hours of free moisture at temperatures between 24° and 28° C. Temperatures between 28° and 32° C. may also be effective. These temperatures are normally encountered during the time period in which dandelion requires treatment. A 12 hour free moisture requirement for infection is common among plant pathogenic fungi. Although the moisture requirement is not seen to be a limitation on the use of the biocontrol agent, since irrigation is often available for turfgrass, it is known in the art that addition of as little as 1–5% vegetable oil or other adjuvant can reduce the free moisture requirement by four hours or more.

The present invention is not intended to be limited to the embodiments and examples presented herein, but rather to encompass all such modifications and variations as come within the scope of the appended claims.

We claim:

1. A substantially pure preparation of an Acremonium fungal strain effective to induce disease in a dandelion plant as measured in a plant disease and mortality assay.

2. A substantially pure preparation of Acremonium sp. ATCC 74368.

3. A method for inducing disease in a dandelion plant, the method comprising the steps of:

administering to the plant an amount of an Acremonium fungus effective to induce disease in the plant as measured in a plant disease and mortality assay at a selected moisture level and temperature; wherein the treated dandelion plant has an increased rate of disease relative to an untreated plant.

4. A composition effective for biocontrol of dandelions comprising:

Acremonium spp. ATCC 74368; and an inert carrier.

* * * * *